(12) United States Patent
Ikeda et al.

(10) Patent No.: US 6,304,813 B1
(45) Date of Patent: Oct. 16, 2001

(54) OXYGEN CONCENTRATION DETECTOR AND METHOD OF USING SAME

(75) Inventors: Shinji Ikeda, Mishima; Yusuke Suzuki, Susono, both of (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 09/517,627

(22) Filed: Mar. 3, 2000

(30) Foreign Application Priority Data

Mar. 29, 1999 (JP) .................................................. 11-086335
Aug. 3, 1999 (JP) .................................................. 11-220254

(51) Int. Cl.[7] .......................... F02D 41/14; G01N 27/409
(52) U.S. Cl. ........................ 701/109; 123/697; 73/23.32; 204/406; 204/425
(58) Field of Search ............................. 123/697; 701/102, 701/103, 109; 73/23.31, 23.32, 117.3; 204/406, 424, 425, 426

(56) References Cited

U.S. PATENT DOCUMENTS

| | | | | |
|---|---|---|---|---|
| 4,851,103 | * | 7/1989 | Usami et al. .......................... | 204/406 |
| 5,148,795 | * | 9/1992 | Nagai et al. .......................... | 123/697 |
| 5,353,774 | * | 10/1994 | Furuya .................................. | 123/697 |
| 5,518,600 | * | 5/1996 | Uchinami ............................. | 204/425 |
| 5,616,835 | * | 4/1997 | Schnaibel et al. ................... | 123/697 |
| 5,836,292 | * | 11/1998 | Aoki ..................................... | 123/697 |
| 5,993,641 | * | 11/1999 | Okazaki et al. ...................... | 204/425 |
| 6,067,841 | * | 5/2000 | Suzuki et al. ........................ | 73/23.32 |

FOREIGN PATENT DOCUMENTS

| | | | | |
|---|---|---|---|---|
| 63-168550-A | * | 7/1988 | (JP) ..................................... | 123/697 |
| 3-229142-A | * | 10/1991 | (JP) ..................................... | 123/697 |
| 08-278279 | | 10/1996 | (JP) . | |
| 2000-74873-A | * | 3/2000 | (JP) ..................................... | 123/697 |

* cited by examiner

Primary Examiner—Willis R. Wolfe
(74) Attorney, Agent, or Firm—Oliff & Berridge, PLC

(57) ABSTRACT

An oxygen concentration detector includes an air-fuel ratio sensor, a heater that heats the air-fuel ratio sensor, a heater controller that supplies electric power to the heater such that the air-fuel ratio sensor reaches an activation temperature, and an element temperature detector that detects a temperature of an element of the air-fuel ratio sensor. The heater controller detects a rate of decrease in the temperature of the element of the air-fuel ratio sensor based on the temperature detected by the element temperature detector, and determines that the sensor element is wetted when the detected rate of decrease is greater than a reference value. The element temperature detector can detect the sensor element temperature based on an impedance of the element. The heater controller can prevent the supply of electric power to the heater if it is determined that the sensor element is wetted. The air-fuel ratio sensor can be provided in an exhaust passage of an engine.

19 Claims, 12 Drawing Sheets

OXYGEN CONCENTRATION DETECTOR AND METHOD OF USING SAME

INCORPORATION BY REFERENCE

The disclosure of Japanese Patent Application Nos. HEI 11-86335 filed on Mar. 29, 1999 and HEI 11-220254 filed on Aug. 3, 1999, including the specifications, drawings and abstracts are incorporated herein by reference in their entirety.

BACKGROUND OF THE INVENTION

1. Field of Invention

The present invention relates to an oxygen concentration detector and methods of using the oxygen concentration detector.

2. Description of Related Art

According to air-fuel ratio control of engines in recent years, an air-fuel ratio sensor and a catalyst are disposed in the exhaust system of the engine, and feedback control is performed such that an air-fuel ratio of exhaust gas detected by the air-fuel ratio sensor becomes equal to a target air-fuel ratio, for example, a stoichiometric air-fuel ratio, with a view to purifying the maximum possible amounts of noxious substances contained in the exhaust gas (such as HC, CO, NOx and the like) by means of the catalyst. As the air-fuel ratio sensor, a λ-type air-fuel ratio sensor (referred to as the $O_2$ sensor) is used. The λ-type air-fuel ratio sensor has a Z-characteristic for determining, based on a concentration of oxygen contained in exhaust gas discharged from the engine, whether an air-fuel ratio of exhaust gas in the engine is rich or lean.

Alternatively, as the air-fuel ratio sensor, a limiting current-type oxygen concentration detecting element for outputting a limiting current proportional to the concentration of oxygen contained in exhaust gas discharged from the engine is used. The limiting current oxygen concentration detecting element detects the air-fuel ratio of exhaust gas in the engine from a concentration of oxygen, over a wide range and linearly. The limiting current oxygen concentration detecting element is effective in enhancing precision of the air-fuel ratio control and in performing control such that an air-fuel ratio of exhaust gas in the engine becomes equal to a target air-fuel ratio over a wide range of rich, stoichiometric and lean air-fuel ratios.

In order to maintain precision in detecting an air-fuel ratio, it is indispensable to keep the aforementioned air-fuel ratio sensor, namely, the $O_2$ sensor or the limiting current type oxygen concentration detecting element, in an activated state. Normally, as soon as the engine is started, a heater attached to the $O_2$ sensor or to the limiting current type oxygen concentration detecting element is supplied with electric power, whereby the sensor or the detecting element is heated and activated at an early stage. Thus, in order to maintain an activated state of the sensor or the detecting element, heater conduction control is performed.

According to a heater control device of an air-fuel ratio sensor disclosed in Japanese Patent Application Laid-Open No. HEI 8-278279, during an initial conduction period for a heater, all the electric power, that is, electric power with a duty ratio of 100%, is supplied to the heater for early activation of an element of the air-fuel ratio sensor, until the heater reaches a predetermined temperature. If the heater reaches the predetermined temperature, electric power corresponding to the temperature of the heater is supplied to the heater. If the sensor element reaches a predetermined temperature, electric power corresponding to the temperature of the element of the air-fuel ratio sensor is supplied to the heater.

However, in the heater control device of the air-fuel ratio sensor disclosed in Japanese Patent Application Laid-Open No. HEI 8-278279 mentioned above, at the time of the cold starting operation of the engine, water that has condensed in a catalyst provided upstream in an exhaust pipe either accumulates in a bottom portion of the exhaust pipe, or sticks to a wall surface of the exhaust pipe. If the exhaust system has not been warmed up at the time of the cold starting operation of the engine, the condensed water splashes together with exhaust gas and passes through small holes in a protector cover attached to the exhaust pipe so as to surround the air-fuel ratio sensor that is disposed downstream of the catalyst in the exhaust pipe. Thus, the sensor element in the protector cover is wetted and quenched, so that a difference in temperature between the heater and the air-fuel ratio sensor increases abruptly. As a result, the element of the air-fuel ratio sensor may crack due to thermal shock. Accordingly, in order to prevent the element from cracking due to thermal shock, it is important to detect a wet condition of the sensor element.

SUMMARY OF THE INVENTION

It is an object of the present invention to enhance precision in detecting a wet condition of a sensor element.

It is another object of the present invention to provide an oxygen concentration detector that prevents an element of an air-fuel ratio sensor from cracking due to the thermal shock resulting from the wetting of the element of the air-fuel ratio sensor when the air-fuel ratio sensor is preheated during, or prior to, the engine starting operation.

According to a first aspect of the present invention, an exemplary embodiment of an oxygen concentration detector includes an air-fuel ratio sensor, a heater that heats the air-fuel ratio sensor, a heater controller that supplies electric power to the heater such that the air-fuel ratio sensor reaches an activation temperature, and an element temperature detector that detects the temperature of an element of the air-fuel ratio sensor. The controller detects a rate of decrease in the element temperature of the air-fuel ratio sensor based on the temperature detected by the element temperature detector, and determines that the sensor element has been wetted when the detected rate of decrease is greater than a reference value. When wetting is detected, the controller controls the supply of electric power to the heater so as to attenuate thermal shock.

According to the first aspect of the present invention, upon detection of wetting of the sensor element, the supply of electric power to the heater is controlled so as to attenuate thermal shock. Therefore, the heater is prevented from being heated abruptly. Thus, the element of the air-fuel ratio sensor is prevented from cracking due to thermal shock resulting from an abrupt increase in the difference in temperature between the heater and the element of the air-fuel ratio sensor.

In the first aspect of the present invention, the element temperature detector can be configured to detect an element temperature of the air-fuel ratio sensor based on an element impedance of the air-fuel ratio sensor.

In the first aspect of the present invention, the heater controller can be configured to prohibit the heater from being supplied with electric power when it is determined that the sensor element has been wetted.

In the first aspect of the present invention, the air-fuel ratio sensor can be disposed in an exhaust passage of an internal combustion engine.

According to a second aspect of the present invention, an exemplary embodiment of an oxygen concentration detector includes an air-fuel ratio sensor provided in an exhaust pipe of an internal combustion engine, a heater that heats the air-fuel ratio sensor and a heater controller that supplies electric power to the heater such that the air-fuel ratio sensor reaches an activation temperature. The controller predicts whether an element of the air-fuel ratio sensor may be wetted, and limits the electric power supplied to the heater if it is predicted that the sensor element may be wetted.

According to the second aspect of the present invention, if it predicted that the sensor element may be wetted, the electric power supplied to the heater is limited. Therefore, the element is prevented from cracking due to thermal shock.

In the second aspect of the present invention, the prediction can based on determining whether water is disposed on a wall surface of the exhaust pipe.

In the second aspect of the present invention, the oxygen concentration detector may include a flow rate controller that reduces a flow rate of exhaust gas in the internal combustion engine when it is determined that the sensor element may be wetted.

Because the flow rate of exhaust gas is thus reduced, the water adhering to the wall surface of the exhaust pipe is inhibited from splashing. As a result, the element of the air-fuel ratio sensor is inhibited from being wetted, which reduces the possibility of the element cracking due to thermal shock.

In the second aspect of the present invention, the controller can determine, based on a temperature of the exhaust pipe, whether or not water is disposed on the wall surface of the exhaust pipe.

In this construction, because water adheres to the wall surface of the exhaust pipe because water vapor in the exhaust pipe condenses, the determination is made based on the temperature of the exhaust pipe. Thus, the precision in detecting whether or not water is disposed on the wall surface of the exhaust pipe is enhanced.

This invention also provides methods of attenuating thermal shock of an element of an air-fuel ratio sensor disposed in an exhaust passage of an engine, such as an internal combustion engine.

BRIEF DESCRIPTION OF THE DRAWINGS

The foregoing and further objects, features and advantages of the present invention will become apparent from the following description of preferred embodiments with reference to the accompanying drawings, wherein.

DETAILED DESCRIPTION OF PREFERRED EMBODIMENTS

Embodiments of the present invention will now be described in detail with reference to the accompanying drawings.

Figure 1:
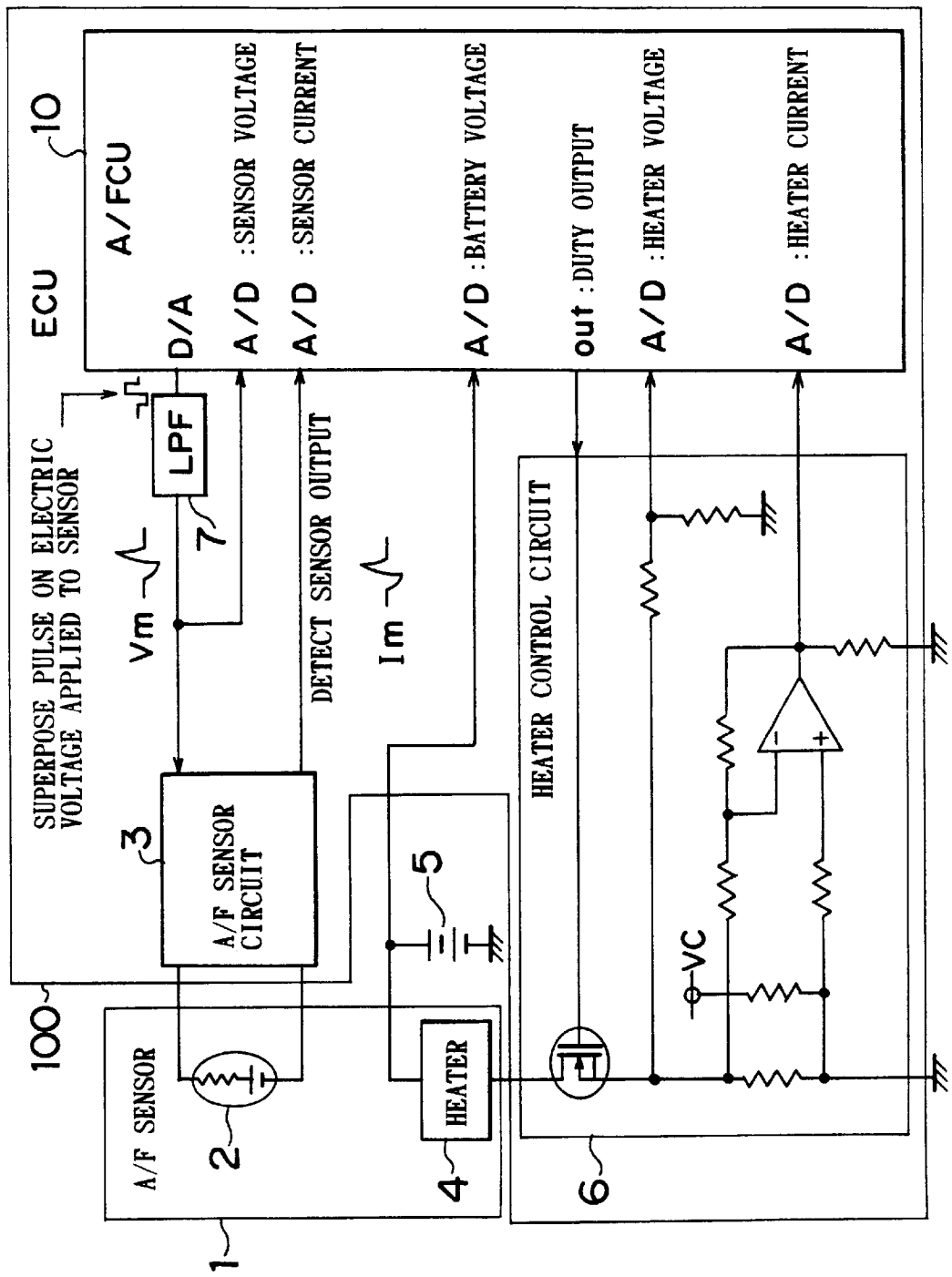
FIG. 1 is a schematic structural view of an oxygen concentration detector according to a first embodiment of the present invention.

FIG. 1 is a schematic structural view of an oxygen concentration detector according to a first embodiment of the present invention. In the other drawings, like components will be denoted by like reference numerals. An air-fuel ratio sensor 1 that detects an exhaust air-fuel ratio of an internal combustion engine (not shown) is disposed in an exhaust passage of the engine and includes an air-fuel ratio sensor element (hereinafter referred to as the "sensor element") 2 and a heater 4. An electric voltage is applied to the sensor element 2 from an air-fuel ratio sensor circuit (hereinafter referred to as the "sensor circuit") 3, and electric power is supplied to the heater 4 from a battery 5 through a heater control circuit 6. The sensor circuit 3 receives an analog impressed voltage from an air-fuel ratio control unit (A/FCU) 10 through a low-pass filter (LPF) 7 and applies the voltage to the sensor element 2.

In combination with the sensor circuit 3, the heater control circuit 6 and the LPF 7, the A/FCU 10 constitutes part of an electronic control unit (ECU) 100. After digital data stored in a D/A converter have been converted into a rectangular analog voltage, the A/FCU 10 outputs the analog voltage to the sensor circuit 3 through the LPF 7. The LPF 7 outputs a smoothed signal, which is obtained by removing high-frequency components from a rectangular analog voltage signal, thus preventing an output current of the sensor element 2 from being detected erroneously due to high-frequency noise. Upon application of the smoothed signal to the sensor element 2, the A/FCU 10 detects an electric current that flows through the sensor element 2 in proportion to a concentration of oxygen in detected gas, namely, exhaust gas, and an electric voltage that is applied to the sensor element 2 at this moment. For the purpose of detecting the electric current and electric voltage, the A/FCU 10 includes A/D converters. These A/D converters receive from the sensor circuit 3 an analog voltage corresponding to an electric current flowing through the sensor element 2 and an electric voltage applied to the sensor element 2, and convert them into digital data.

Unless the sensor element 2 is activated, it is impossible to use an output from the air-fuel ratio sensor 1 for air-fuel ratio control. Hence, at the time of the engine starting operation, the A/FCU 10 supplies electric power to the heater 4 installed in the sensor element 2 from the battery 5 and causes an electric current to flow through the heater 4, thus activating the sensor element 2. After the sensor element 2 has been activated, the A/FCU 10 supplies electric power to the heater 4 so as to maintain the activated state of the sensor element 2. An electric voltage of the battery 5 is converted into digital data by an A/D converter provided in the A/FCU 10.

Thus, in view of the fact that the resistance of the sensor element 2 changes in accordance with its temperature, namely, the resistance of the sensor element 2 decreases in accordance with an increase in sensor element temperature, electric power is supplied to the heater 4 such that the resistance of the sensor element 2 becomes equal to a resistance value corresponding to a temperature for maintaining an activated state of the sensor element 2. For example, the resistance can be about 30Ω. Thereby the temperature of the sensor element 2 can be controlled to be maintained at a selected value, for example, at 700° C. The air-fuel ratio control unit (A/FCU) 10 further includes an A/D converter. This A/D converter receives analog voltages corresponding to an electric voltage and an electric current of the heater 4 from the heater control circuit 6 for heating the sensor element 2, and converts the analog voltages into digital data. These digital data are used, for example, to calculate a resistance value of the heater 4. Electric power corresponding to an operating condition of the engine is supplied to the heater 4 based on the calculated resistance value. Then, the temperature of the heater 4 is controlled so as to prevent an excessive rise in temperature (OT: over temperature) of the heater 4. In some exemplary embodiments of the present invention, an oxygen concentration detecting element of a limiting current type is used as the air-fuel ratio sensor 1. However, the present invention is not limited to such a sensor and also can be applied in exemplary embodiments where a λ-type air-fuel ratio sensor (referred to as an $O_2$ sensor), having a Z-characteristic for determining whether the air-fuel ratio is rich or lean, is used as the air-fuel ratio sensor 1.

The air-fuel ratio control unit (A/FCU) 10 includes a CPU, a ROM, a RAM, a B (battery back-up) RAM, an input port, an output port, A/D converters and a D/A converter, which are interconnected to one another, for example, by a bi-directional bus. The A/FCU 10 performs heater control of the air-fuel ratio sensor 1 of the present invention, which will be described below. A coolant temperature sensor (not shown) for detecting a coolant temperature THW of the engine is connected to one of the A/D converters in the A/FCU 10. The CPU typically reads the coolant temperature THW at intervals of a predetermined period.

The reason why the element of the air-fuel ratio sensor cracks at the time of cold starting operation in known devices will be described hereinafter, with reference to two different types of air-fuel ratio sensors as examples.

Figure 2:
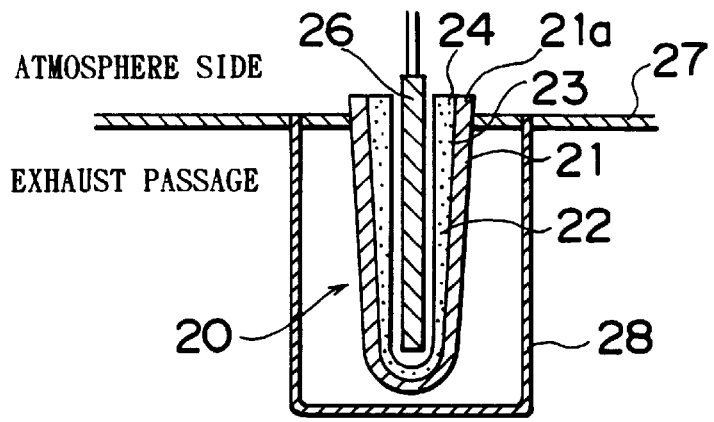
FIG. 2 is a cross-sectional view of a cup-type air-fuel ratio sensor.

FIG. 2 shows a cup-type air-fuel ratio sensor. The sensor includes a sensor body 20 having a diff-used resistor layer 21 of a cup-shaped cross-section. The diffused resistor layer 21 is securely fitted at an opening end 21a thereof into a mounting hole portion of an exhaust pipe 27 of the engine. The diffused resistor layer 21 is formed, for example, by plasma spray coating $ZrO_2$ or the like.

The sensor body 20 has a solid electrolyte layer 22, which is uniformly fitted into and fixed to an inner periphery wall of the diffused resistor layer 21 through an exhaust-side electrode layer 23 of a cup-shaped cross-section by an oxygen ion conductive sintered oxide. An atmosphere-side electrode layer 24 of a cup-shaped cross-section is uniformly adhered to an inner surface of the solid electrolyte layer 22. In this configuration, both the exhaust-side electrode layer 23 and the atmosphere-side electrode layer 24 are formed by subjecting a noble metal of high catalytic activity, such as platinum (Pt), to chemical plating or the like to achieve sufficient porosity. The exhaust-side electrode layer 23 has an area of about 10 to 100 mm$^2$ and a thickness of about 0.5 to 2.0 μm. The atmosphere-side electrode layer 24 has an area of 10 mm$^2$ or more and a thickness of about 0.5 to 2.0 μm. The sensor body 20 is surrounded by a protector cover 28. The protector cover 28 provides heat insulation of the sensor body 20 while preventing the sensor body 20 from directly contacting exhaust gas. The protector cover 28 has a multitude of small holes that allow communication between the interior and exterior of the cover.

At the time of cold starting operation of the engine, substantial electric power needs to be supplied to the heater 26 so as to heat the sensor body 20 at an early stage. Therefore, according to the related art, the battery 5 supplies electric power to the heater 26 with a duty ratio of 100%. Water that has condensed in a catalyst provided upstream in the exhaust pipe 27 accumulates in a bottom portion of the exhaust pipe 27 or adheres to a wall surface of the exhaust pipe. If the exhaust system has not been warmed up at the time of the cold starting operation of the engine, the condensed water splashes together with exhaust gas and passes through the small holes of the protector cover 28, thus quenching the sensor body 20. Consequently, the element of the sensor body 20 is cracked.

Figure 3:
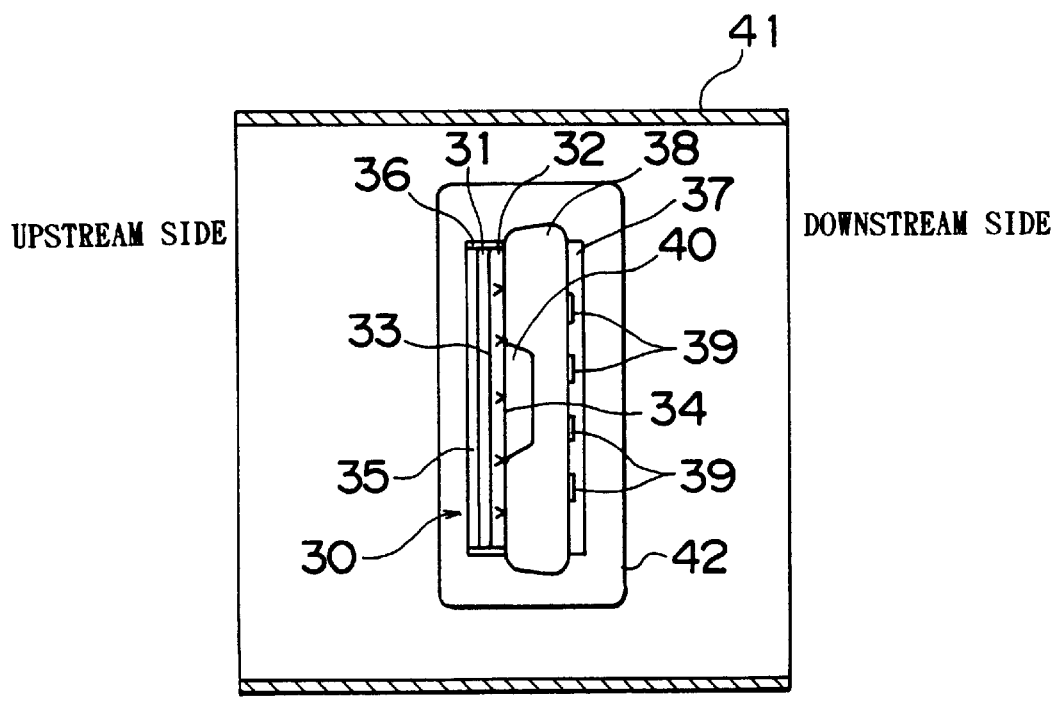
FIG. 3 is a cross-sectional view of a lamination-type air-fuel ratio sensor.

FIG. 3 is a cross-sectional view of a lamination-type air-fuel ratio sensor. The lamination-type air-fuel ratio sensor is disposed downstream of a catalyst (not shown) in the exhaust pipe. A sensor body 30 of the lamination-type air-fuel ratio sensor is formed by layering a porous diffused resistor layer 31 composed of $Al_2O_3$, a solid electrolyte layer 32 composed of $ZrO_2$, an exhaust-side electrode layer 33 interposed between the resistor layer 31 and the electrolyte layer 32, an atmosphere-side electrode layer 34 facing the atmosphere side of the solid electrolyte layer 32, and a shielding layer 35 composed of $Al_2O_3$ and provided so as to face the exhaust side to ensure heat insulation of the sensor body 20. Both the exhaust-side electrode layer 33 and the atmosphere-side electrode layer 34 are formed by subjecting a noble metal of high catalytic activity, such as platinum (Pt), to chemical plating or the like to achieve sufficient porosity. The sensor body 30 has a poisoning substance trapping layer 36 surrounding the aforementioned respective layers. The poisoning substance trapping layer 36 traps noxious components contained in the exhaust gas. The sensor body 30 includes a heater 38 composed of Pt on a heater substrate 37. The heater substrate 37 is attached to a duct 39 which is also composed of $Al_2O_3$. The duct 39 supports a laminated body of the sensor body 30 through an atmosphere introduction hole 40 that communicates with the atmosphere, and is fixed to an exhaust pipe 41. The sensor body 30 is surrounded by a protective cover 42. The protective cover 42 provides heat insulation of the sensor body 30 while preventing the sensor body 30 from directly contacting the exhaust gas. The protective cover 42 has a multitude of small holes that allow communication between the interior and exterior of the cover.

At the time of cold starting operation of the engine, substantial electric power needs to be supplied to the heater 38 so as to heat the sensor body 30 at an early stage. Therefore, according to the related art, the battery 5 supplies electric power to the heater 38 with a duty ratio of 100%. Water condensed in a catalyst provided upstream in the exhaust pipe 41 accumulates in a bottom portion of the exhaust pipe 41 or adheres to a wall surface of the exhaust pipe. If the exhaust system has not been warmed up at the time of cold starting operation of the engine, the condensed water splashes together with exhaust gas and passes through the small holes of the protector cover 42, thus quenching the sensor body 30. Consequently, the element of the sensor body 30 is cracked.

In order to prevent the air-fuel ratio sensors described with reference to FIGS. 2 and 3 from cracking at the time of the cold starting operation of the engine, according to the present invention, wetting of the sensor element is detected and control of the heater 4 is performed, so as to inhibit or prevent an electric current from flowing through the heater 4. This will be described below.

Figure 4:
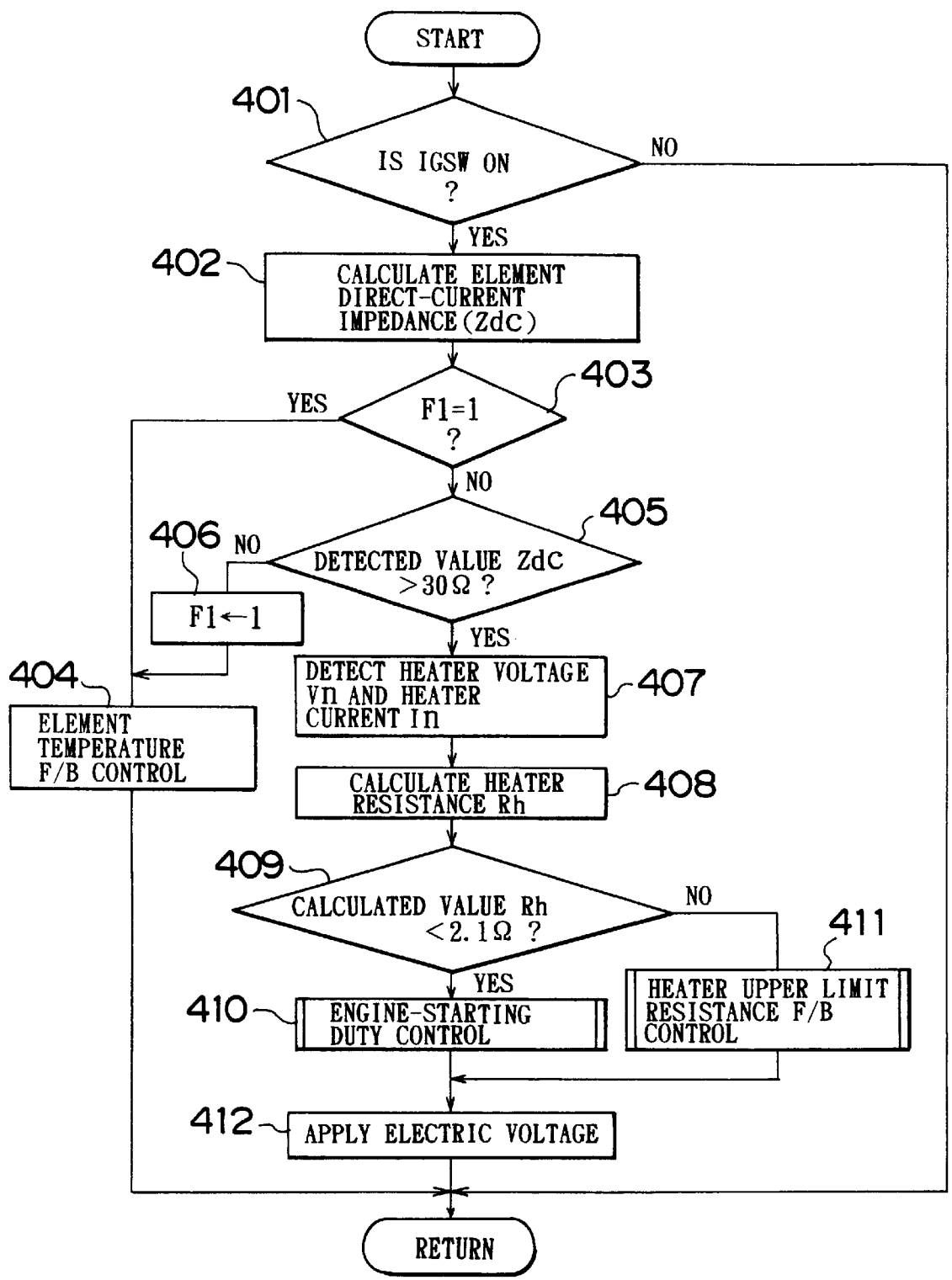
FIG. 4 is a flowchart of an exemplary heater control routine.
Figure 5:
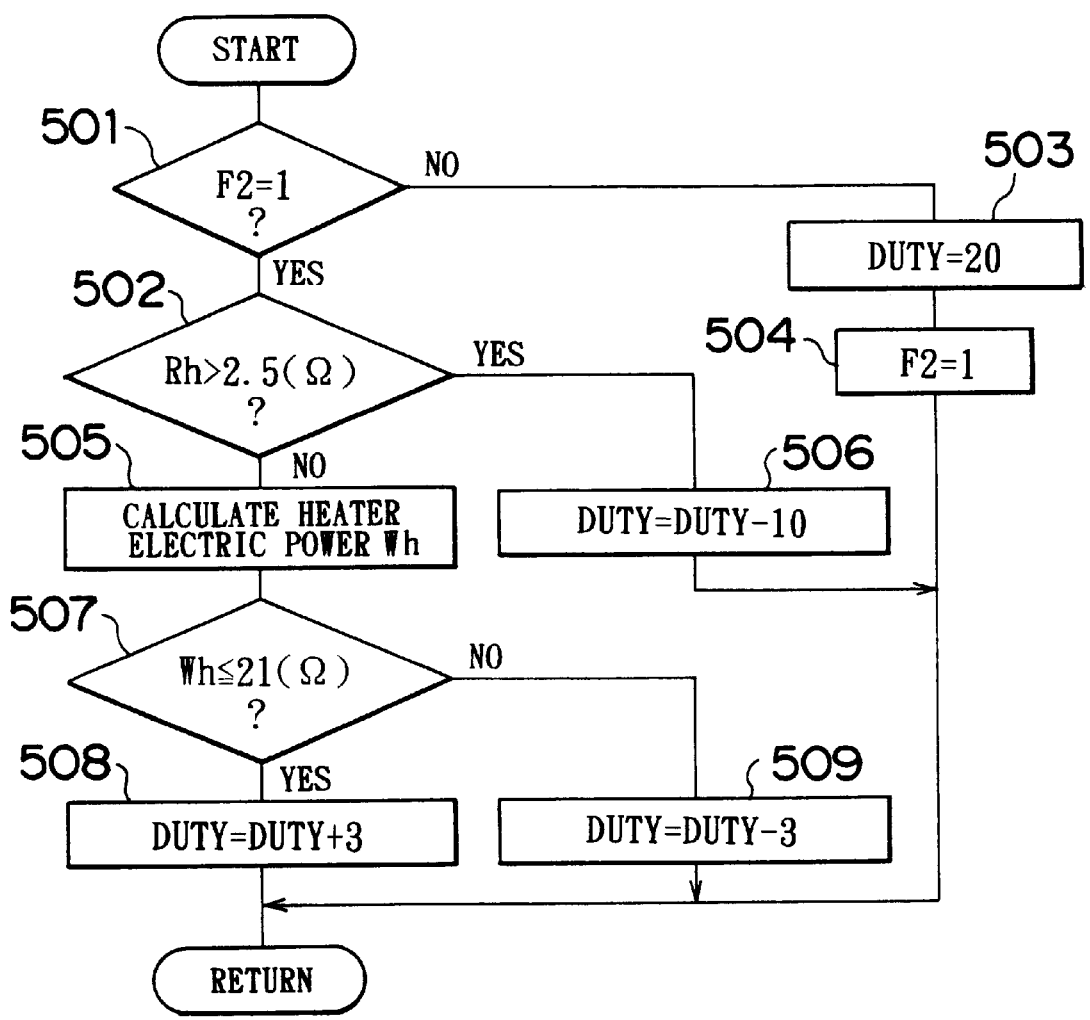
FIG. 5 is a flowchart of exemplary heater control based on an upper limit resistance of a heater.
Figure 6:
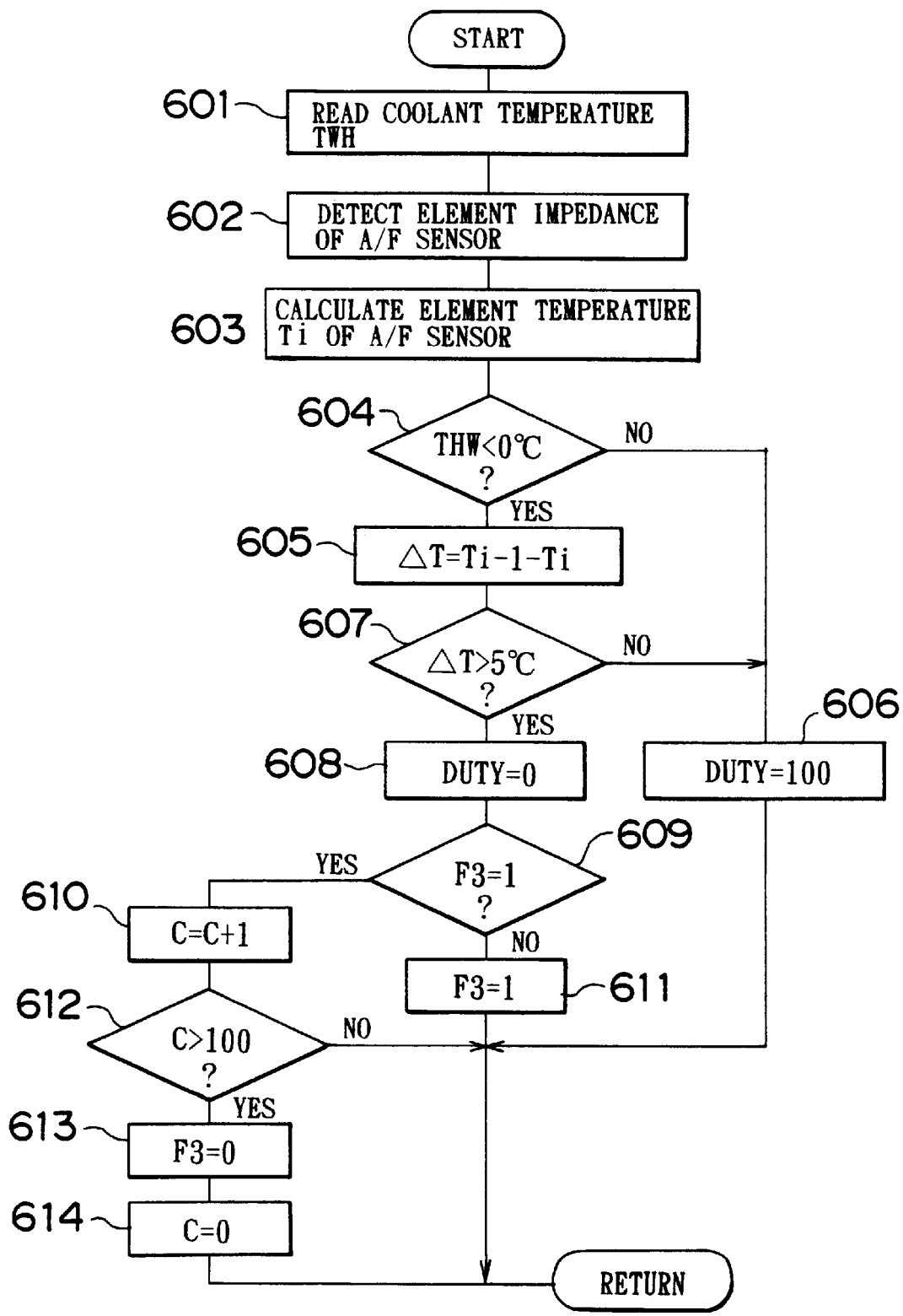
FIG. 6 is a flowchart of exemplary heater control at the time of engine starting operation.

FIG. 4 is a flowchart of an exemplary embodiment of a heater control routine. Processing in this routine and flowcharts shown in FIGS. 5 and 6 are performed at intervals of a predetermined period, for example, 64 ms. First, it is determined in step 401 whether an ignition switch IGSW (not shown) is on or off. If the IGSW is on, the operation proceeds to step 402. If the IGSW is on, this routine is terminated.

Processing in steps 402 through 412 will now be described. For early activation of the air-fuel ratio sensor 1, the battery 5 starts supplying electric power to the heater 4, and electric power set in accordance with duty control at the time of engine starting operation is supplied to the heater 4 until the heater temperature reaches a predetermined temperature (engine-starting DUTY control). If the heater temperature reaches the predetermined temperature, electric power corresponding to the heater temperature is supplied to the heater 4 (heater upper limit resistance F/B control). If the temperature of the air-fuel ratio sensor 1 reaches a predetermined temperature, electric power for maintaining an activated state of the sensor element 2 in accordance with an element temperature of the air-fuel ratio sensor 1 is supplied to the heater 4 (element temperature F/B control).

In step 402, an element direct-current impedance Zdc of the air-fuel ratio sensor 1 is calculated. The impedance Zdc is calculated by detecting an electric current Ineg at the time of application of a negative voltage Vneg to the sensor element 2 according to the following formula: Zdc=Vneg/Ineg. In general, the element direct-current impedance decreases in accordance with a rise in element temperature. For example, if the sensor element 2 has an activation temperature of 700° C., the element direct-current impedance is 30Ω.

It is determined in step 403 whether or not an activation flag F1 of the air-fuel ratio sensor 1 has been set. If F1=1, the operation proceeds to step 404 where the later-described element temperature F/B control is performed. If F1=0, the operation proceeds to step 405.

In step 405, it is determined based on the element direct-current impedance whether or not the sensor element 2 has been activated. That is, if Zdc≦30Ω(NO in step 405), it is determined that the sensor element 2 has been activated, and the activation flag F1 of the air-fuel ratio sensor 1 is set to 1 in step 406. The element temperature F/B control is then performed in step 404. If Zdc>30Ω(YES in step 405), it is determined that the sensor element 2 has not been activated, and the operation proceeds to step 407 where heater control for activating the sensor element 2 is performed. The flag F1 is reset by a one-shot pulse signal when the ignition switch IGSW is switched from off to on.

In step 407, an electric voltage Vn applied to the heater 4 and an electric current In flowing through the heater 4 are detected.

In step 408, a resistance Rh of the heater 4 is calculated according to the following formula: Rh=Vn/In.

It is determined in step 409 whether or not the heater temperature is below a heater upper limit temperature, such as, for example, 1020° C., which is lower than a heat-resistant threshold temperature, such as, for example, 1200° C. by a predetermined temperature. If the result in step 409 is YES, the operation proceeds to step 410 where DUTY control for supplying the greatest possible electric power to the heater 4 is performed. If the result in step 409 is NO, the operation proceeds to step 411 where control for maintaining the heater 4 at the heater upper limit temperature 1020° C. is performed. The processing in step 410 and step 411 will later be described in detail with reference to FIGS. 6 and 5, respectively. The heater upper limit temperature is not set to the heat-resistant threshold temperature because the resistance-temperature characteristic of the heater 4 is inconsistent. By using a median of dispersed values, it is determined that the heater resistance Rh corresponding to the heater upper limit temperature 1020° C. is 2.1Ω. When the heater control is performed so that the heater resistance becomes equal to 2.1Ω, the dispersion of the heater temperature remains within a range of 870 to 1200° C., and the heater temperature does not exceed the heat-resistant threshold temperature of the heater 4.

In step 412, an electric voltage of the battery 5 is applied to the heater in accordance with a DUTY ratio that has been set in step 410 or step 411. As for the DUTY control mentioned above, it is assumed that the operation of applying an electric voltage of the battery 5 to the heater 4 is switched on and off at intervals of, for example, 100 ms. In this case, if the DUTY ratio is 20%, the on-period is 20 ms and the off-period is 80 ms. If the DUTY ratio is 50%, the on-period is 50 ms and the off-period is 50%. If the DUTY ratio is 100%, the on-period is 100 ms. In this manner, the electric voltage of the battery 5 is applied to the heater 4. Next, the processing in step 411 in FIG. 4 will be described in detail with reference to FIG. 5.

FIG. 5 shows heater control based on an upper limit resistance of the heater. First, it is determined in step 501 whether or not a heater electric power control flag F2, indicating that the heater electric power control is being performed, has been set. If F2=1, the operation proceeds to step 502. If F2=0, the operation proceeds to step 503 where an initial duty ratio of the heater electric power control is set to 20%, which is a value that is selected so as to inhibit the heater temperature from changing abruptly at the time of a transition from the heater electric voltage control to the heater electric power control. Then in step 504, the flag F2 is set. The flag F2 is reset by a one-shot pulse signal when the ignition switch IGSW is switched from off to on.

In order to perform control for protecting the heater 4 from being heated abnormally due to a rise in exhaust temperature or the like upon sudden change of operating conditions of the engine, it is determined in step 502 whether or not the heater resistance Rh is greater than 2.5Ω. If Rh>2.5Ω, the operation proceeds to step 506. If Rh<2.5Ω, the operation proceeds to step 505. In step 506, a calculation is made according to the formula: DUTY=DUTY−10, and a new DUTY ratio is set to the calculated value. If the value of DUTY has become negative, it is set to 0.

In step 505, the heater electric power Wh is calculated according to the following formula.

Wh=Vn×In×DUTY /100

In this formula, Vn and In are the electric voltage and the electric current, respectively, detected in step 407 in FIG. 4, and DUTY is a DUTY ratio set in step 503, 506, 508 or 509 during the last processing period.

In step 507, the heater electric power Wh during the current processing period is compared with a heater supply power 21 W corresponding to the heat-resistant threshold temperature 1200° C. of the heater 4. If Wh≦21, it is determined that the electric power supplied to the heater 4 is smaller than a target electric power, and the operation proceeds to step 508. In step 508, the duty ratio is increased by 3% (the calculation is made according to a formula DUTY=DUTY+3) so that the electric power supplied to the heater 4 increases. If Wh>21, it is determined that the electric power supplied to the heater 4 is greater than the target electric power, and the operation proceeds to step 509. In step 509, the duty ratio is reduced by 3% (the calculation is made according to a formula DUTY=DUTY−3) so that the electric power supplied to the heater 4 decreases.

The heater control is performed based on the value of DUTY set as described above, which makes it possible to perform control such that the actual electric power supplied to the heater 4 becomes equal to the target electric power 21W.

Next, the element temperature F/B control performed in step 404 will be described.

Based on the element direct-current impedance Zdc detected in step 403, the duty ratio of the electric voltage applied to the heater 4 is calculated according to the following equations such that the element direct-current impedance Zdc becomes equal to 30Ω, which corresponds to an element temperature of 700° C.

DUTY=GP+GI+c;

GP=a (Zdc−30)... proportional term; and

GI=GI+b (Zdc−30)... integrating term.

In the above three equations, a, b and c are constants which are equal to, for example, 4.2, 0.2 and 20, respectively. By controlling the heater 4 with the thus-calculated duty ratio, the element direct-current impedance Zdc can be set to a value in the vicinity of 30Ω. Thus, the sensor element can always be maintained in a well-activated state, and the sensor element can be prevented from breaking due to excessive heating. Next, the processing in step 410 in FIG. 4 will be described with reference to FIG. 6.

FIG. 6 is a flowchart of an example of the heater control at the time of engine starting operation. First of all, a coolant temperature THW of the engine is read in step 601. In step 602, an element impedance of the air-fuel ratio sensor is detected. In detecting the element impedance, although an element direct-current impedance may be detected as in step 402 in FIG. 4, an element alternating-current impedance is detected in this case in the following manner.

Normally, an electric voltage, for example, of 0.3 V is applied to the sensor element 2, and a limiting current is detected at intervals of a predetermined period so as to calculate the air-fuel ratio of exhaust gas. The alternating-current impedance Zac is calculated by detecting an electric voltage Vac and an electric current Iac of the sensor element 2 at the time of application of a pulse voltage of 0.3±0.2 V to the sensor element 2 at intervals of, for example, 64 ms, according to a formula Zac=Vac/Iac. In general, the element alternating-current impedance decreases in accordance with a rise in element temperature. In detecting the element alternating-current impedance, there is no need to apply a negative voltage to the sensor element 2 as in the case where an element direct-current impedance is detected. Therefore, the detection of the element alternating-current impedance is advantageous in that the control circuit can be simplified.

Figure 7:
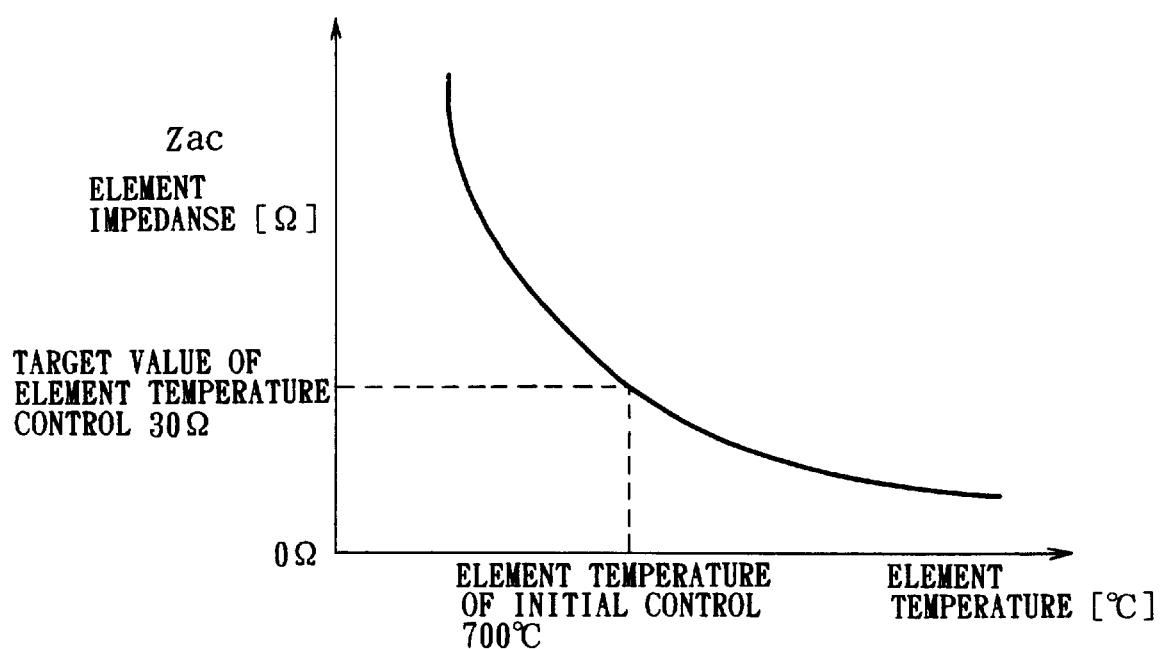
FIG. 7 illustrates an element temperature versus sensor element impedance.

In step 603, the element temperature Ti of the air-fuel ratio sensor during the current processing period is calculated from the impedance Zac of the sensor element detected in step 602 based on the graph shown in FIG. 7.

It is determined in step 604 whether or not the coolant temperature THW read in step 601 is lower than 0° C. If THW<0° C., it is determined that the engine is in the cold starting operation and the operation proceeds to step 605. If THW≧0° C., it is determined that the engine has been warmed up and that the sensor element 2 is not wetted. The operation then proceeds to step 606.

In step 605, the element temperature $T_i$ calculated during the current processing period is subtracted from an element temperature $T_{i-1}$ calculated during the last processing period (ΔT=$T_{i-1}$ $T_i$). In this formula, ΔT represents the decrease in element temperature of the air-fuel ratio sensor per unit time. It is determined in step 607 whether or not the subtraction value ΔT is greater than 5° C. If ΔT>5° C., it is determined that the sensor element 2 has been wetted, and the operation proceeds to step 608. If ΔT≦5° C., it is determined that the sensor element 2 has not been wetted, and the operation proceeds to step 606. When the aforementioned subtraction value ΔT, namely, the degree of decrease in element temperature of the air-fuel ratio sensor per unit time is greater than the reference value 5° C., if the same electric power as during the last processing period is supplied to the heater 4, the sensor element cracks because of the thermal shock resulting from the wetting of the sensor element 2. In order to prevent the sensor element 2 from cracking, the setting of DUTY=0 is carried out in step 608. On the other hand, because it is determined that the sensor element 2 has not been wetted, the setting of DUTY=100 is carried out in step 606 so as to supply all the electric power to the heater 4 for early activation of the sensor element 2.

As described with reference to steps 602 and 603 in FIG. 6, the element temperature of the air-fuel ratio sensor is calculated from its element impedance. However, as for the lamination-type air-fuel ratio sensor, because the heater is located close to the sensor element, the element temperature of the air-fuel ratio sensor can be estimated by detecting the resistance of the heater and calculating the temperature of the heater from the resistance of the heater.

Figure 8:
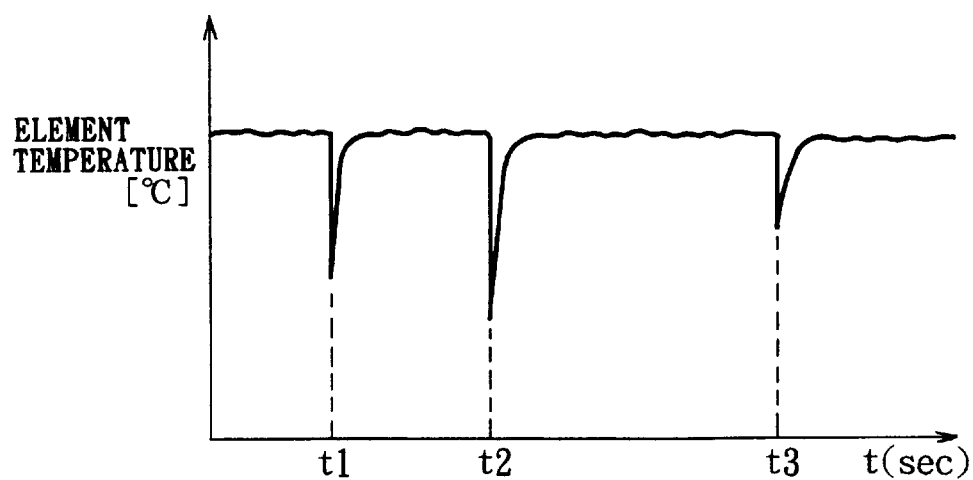
FIG. 8 illustrates the change in element temperature at the time of engine starting operation.

FIG. 8 is a time chart showing how the element temperature changes at the time of engine starting operation. As shown in FIG. 8, if the sensor element 2 is wetted at a time t1, t2 or t3, the temperature of the sensor element 2 falls abruptly. The inventors of the present application have discovered this problem and invented a solution to this problem that prevents electric power from being supplied to the heater 4 upon wetting of the sensor element 2 so as to prevent the sensor element from cracking due to thermal shock, by carrying out the above-mentioned processing in steps 605, 607 and 608.

In step 608, the setting of DUTY=0 is carried out. However, as long as electric power that does not cause the cracking of the sensor element for early activation of the sensor element 2 is supplied to the heater 4, the setting of, for example, DUTY=20 may be carried out in step 608.

Next, processing in steps 609 through 614 will be described. In steps 609 through 614, the length of time from detection of the wetting of the sensor element 2 to restoration of the DUTY control during the normal engine starting operation is set. It is determined in step 609 whether or not a flag F3 indicating that the sensor element 2 is determined to have been wetted has been set. If F3=1, the operation proceeds to step 610. If F3=0, the operation proceeds to step 611. Because it has been determined in step 607 that the sensor element 2 is wetted, the flag F3 is set in step 611.

In step 610, a counter C for measuring the length of time that has elapsed since the setting of F3=1 is counted up (C=C+1). It is determined in step 612 whether or not 6400 ms, that is, 6.4 seconds has elapsed since the setting of F3=1. If the result in step 612 is YES, the operation proceeds to step 613. If the result in step 612 is NO, the present routine is terminated. In step 613, the flag F3 is reset (F3=0). In step 614, the counter C is reset (C=0).

Because of the aforementioned processing in steps 609 through 614, the normal engine-starting DUTY control can be restored after the lapse of 6.4 seconds since determination of the wetting of the sensor element 2. Every time the sensor element is determined to have been wetted, the heater 4 is prevented from being supplied with an electric current for 6.4 seconds.

According to the above-mentioned first embodiment of the present invention, the wetting of the sensor element can be determined based on a sudden decrease in the temperature of the sensor element. Therefore, by taking a measure against the cracking of the element after determination of the wetting of the sensor, or storing a result of determination on the wetting of the sensor element, it is possible to check whether or not the sensor is wetted, and to take measures that prevent cracking of the element. Thus, the first embodiment of the present invention contributes to the specification of a cause of the cracking of the element.

Also, because the temperature of the sensor element is detected based on the element impedance, a temperature sensor for detecting a temperature of the sensor element can be dispensed with.

Further, because the heater is prevented from being supplied with electric power upon detection of the wetting of the sensor element, it is possible to prevent the element of the air-fuel ratio sensor from cracking due to thermal shock resulting from the wetting of the sensor element.

Even if the air-fuel ratio sensor is highly subject to wetting and disposed in an exhaust passage of an internal combustion engine where the occurrence of watering cannot be seen from outside, it is possible to easily detect wetting of the sensor element and easily prevent the element from cracking due to the wetting.

Next, a second embodiment of the present invention will be described with reference to FIGS. 9 through 11. The same components as in the aforementioned first embodiment will be denoted by the same reference numerals and will not be described again.

As in the first embodiment, an oxygen concentration detector according to the second embodiment also has the construction shown in FIG. 1. The second embodiment employs the cup-type air-fuel ratio sensor, as shown in FIG. 2. However, the lamination-type air-fuel ratio sensor shown in FIG. 3 can also be employed in the second embodiment.

Figure 9:
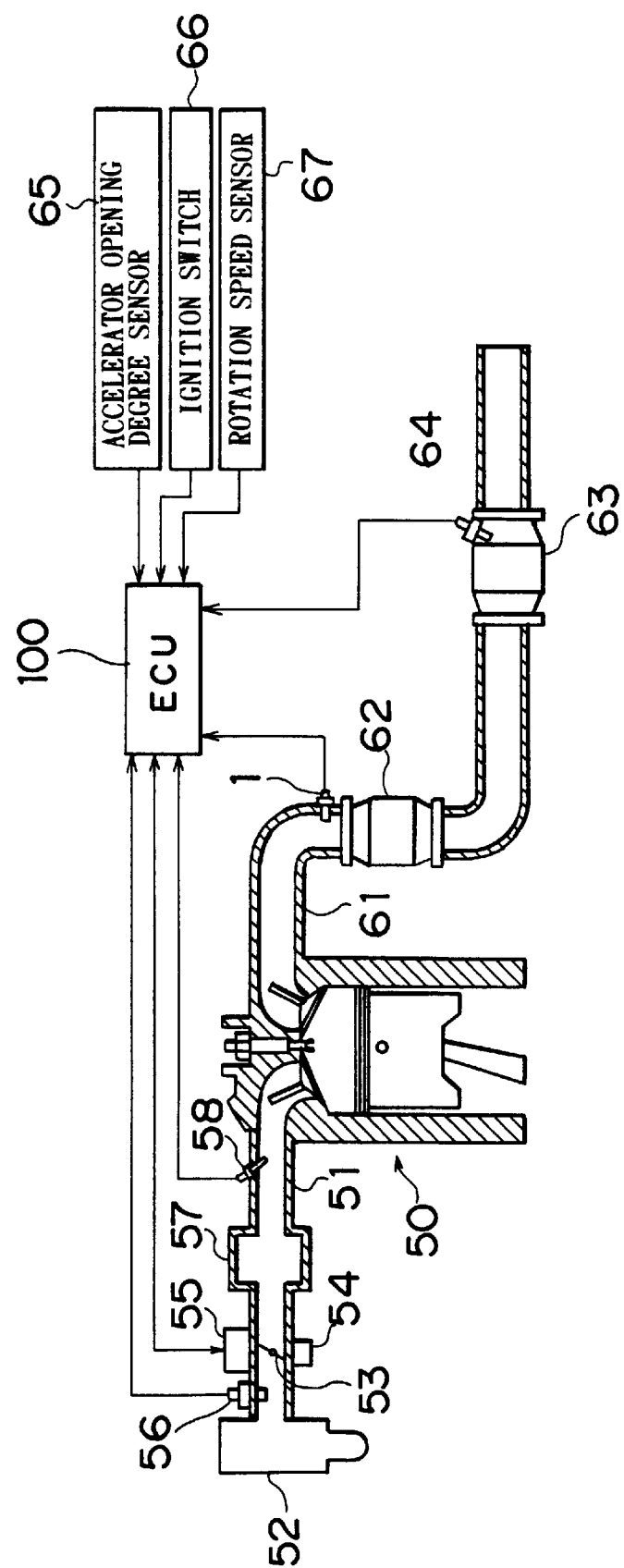
FIG. 9 illustrates an internal combustion engine in which an exemplary embodiment of an oxygen concentration detector according to a second embodiment of the present invention is installed.

FIG. 9 is a structural view of an internal combustion engine in which the oxygen concentration detector shown in FIG. 1 is installed. As shown, in an intake passage 51 of an internal combustion engine (hereinafter referred to simply as the engine) 50, a throttle valve 53 is disposed downstream of an air cleaner 52. A throttle motor 54, which is an actuator for driving the throttle valve 53, is provided at one end of a shaft of the throttle valve 53. A throttle opening degree sensor 55 for detecting an opening degree of the throttle valve 53 is provided at the other end of the shaft of the throttle valve 53. That is, the throttle valve 53 of the second embodiment is an electronic control throttle (hereinafter referred to simply as the electronic throttle) that is driven by the throttle motor 54 to be opened and closed. In the electronic throttle, upon inputting of a command value for the opening degree of the throttle valve 53, the throttle motor 54 causes the throttle valve 53 to open to an opening degree corresponding to the command value.

An intake air temperature sensor 56 is disposed between the throttle valve 53 in the intake passage 51 and the air cleaner 52, and a surge tank 57 is disposed downstream of the throttle valve 53. Furthermore, a fuel injection valve 58 that supplies pressurized fuel from a fuel supplying system to an intake port for each cylinder is provided downstream of the surge tank 57. Outputs from the throttle opening degree sensor 55 and the intake air temperature sensor 56 are inputted to an ECU (engine control unit) 100 in which a microcomputer is installed.

Three-way catalytic converters 62 and 63 for simultaneously purifying three noxious substances contained in exhaust gas, namely, HC, CO and Nox, are provided in an exhaust pipe 61. The three-way catalytic converter 62 is an electrically heated catalyst (EHC) that can be activated at an early stage by electric heating. The three-way catalytic converter 63 is a main catalyst that is activated by the temperature of exhaust gas. The air-fuel ratio sensor 1 is provided upstream of the EHC 62 in the exhaust pipe 61. The air-fuel ratio sensor 1 generates an electric signal corresponding to a concentration of oxygen in the exhaust gas. An exhaust gas temperature sensor 64 is provided near the downstream side of the main catalyst 63 in the exhaust pipe 61. Outputs from the air-fuel ratio sensor 1 and the exhaust gas temperature sensor are inputted to the ECU 100.

Furthermore, an accelerator pedal depression amount signal (an accelerator opening degree signal) from an accelerator opening degree sensor 65 attached to an accelerator pedal (not shown) to detect a depression amount of the accelerator, a key-position signal (an off-position, an on-position and a starter position) from an ignition switch 66 connected to a positive terminal of the battery 5, and a pulse signal outputted from a rotational speed sensor 67 that detects a rotational speed of a ring gear (not shown) of an engine 50 to detect an engine rotational speed NE are inputted to the ECU 100.

Electric control of the oxygen concentration detector according to the second embodiment of the present invention will now be described. In order to prevent the element of the air-fuel ratio sensor from cracking at the time of the cold starting operation of the engine as described with reference to FIGS. 2 and 3, according to the present invention, adhesion of water to the wall surface of the exhaust pipe is detected, and electric conduction control of the heater 4 is performed so as to inhibit or prevent the heater 4 from being supplied with electric power.

Figure 10:
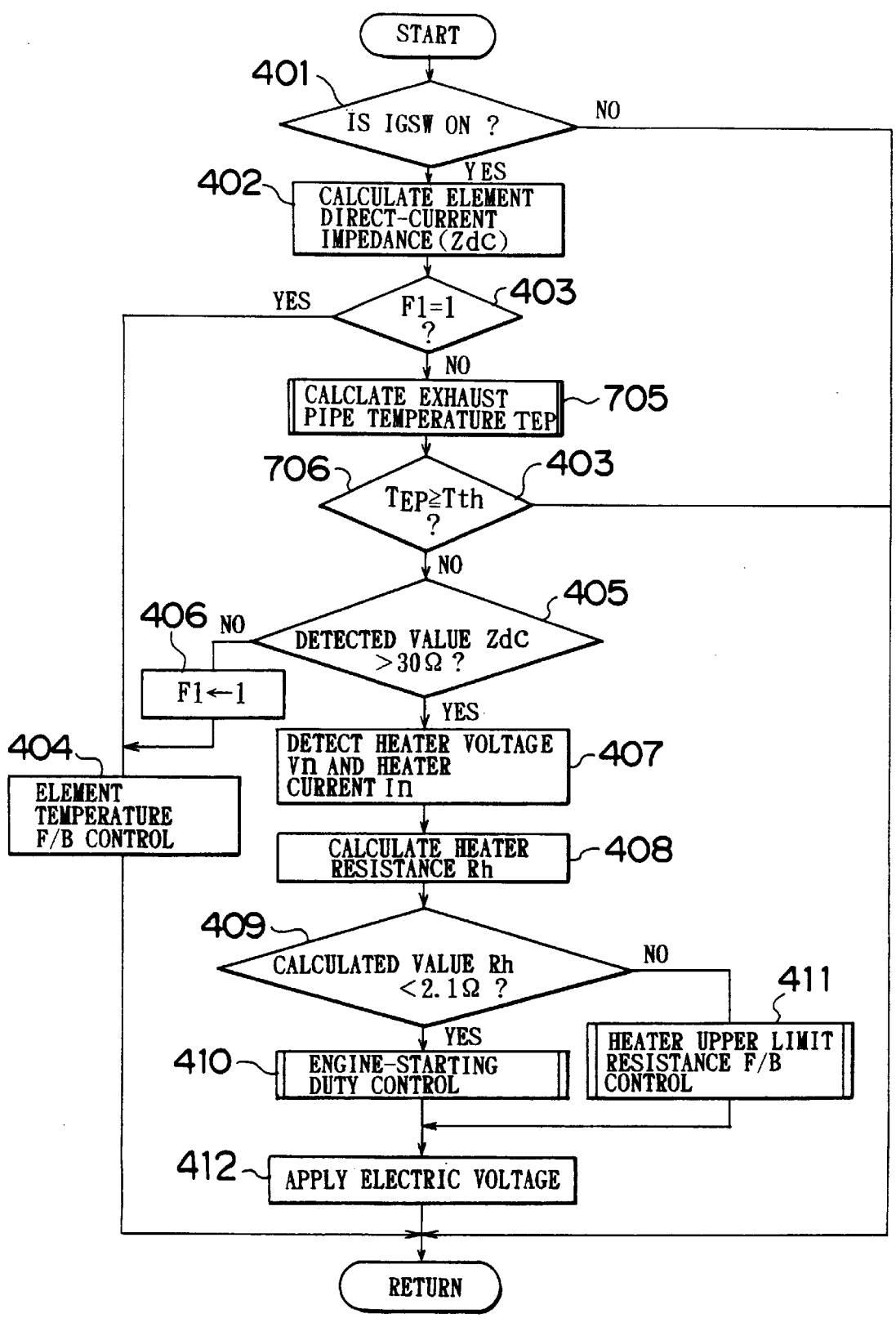
FIG. 10 is a flowchart of an exemplary heater control routine according to the second embodiment of the present invention.
Figure 12:
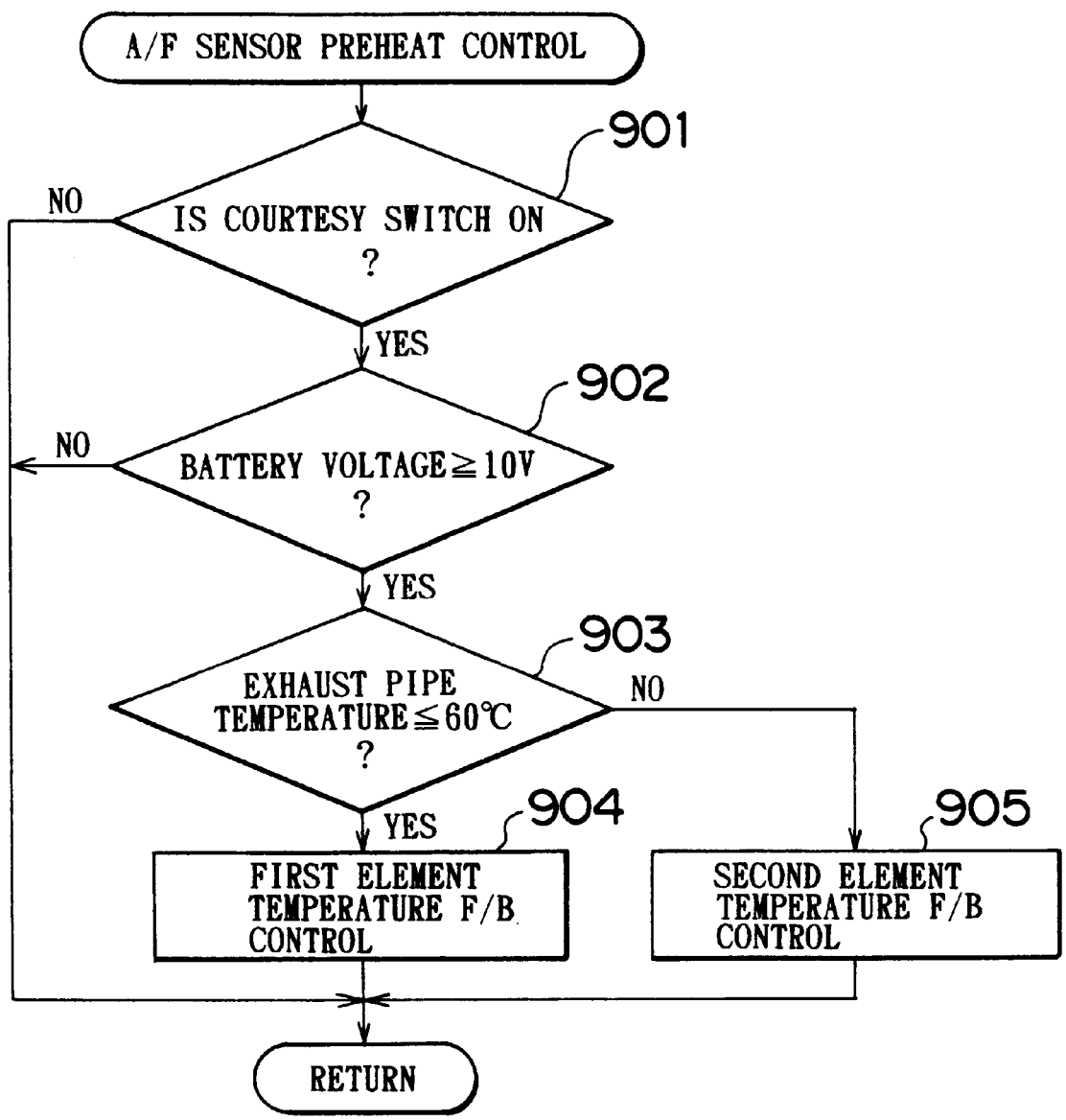
FIG. 12 is a flowchart of an exemplary preheat control routine of an air-fuel ratio sensor.
Figure 13:
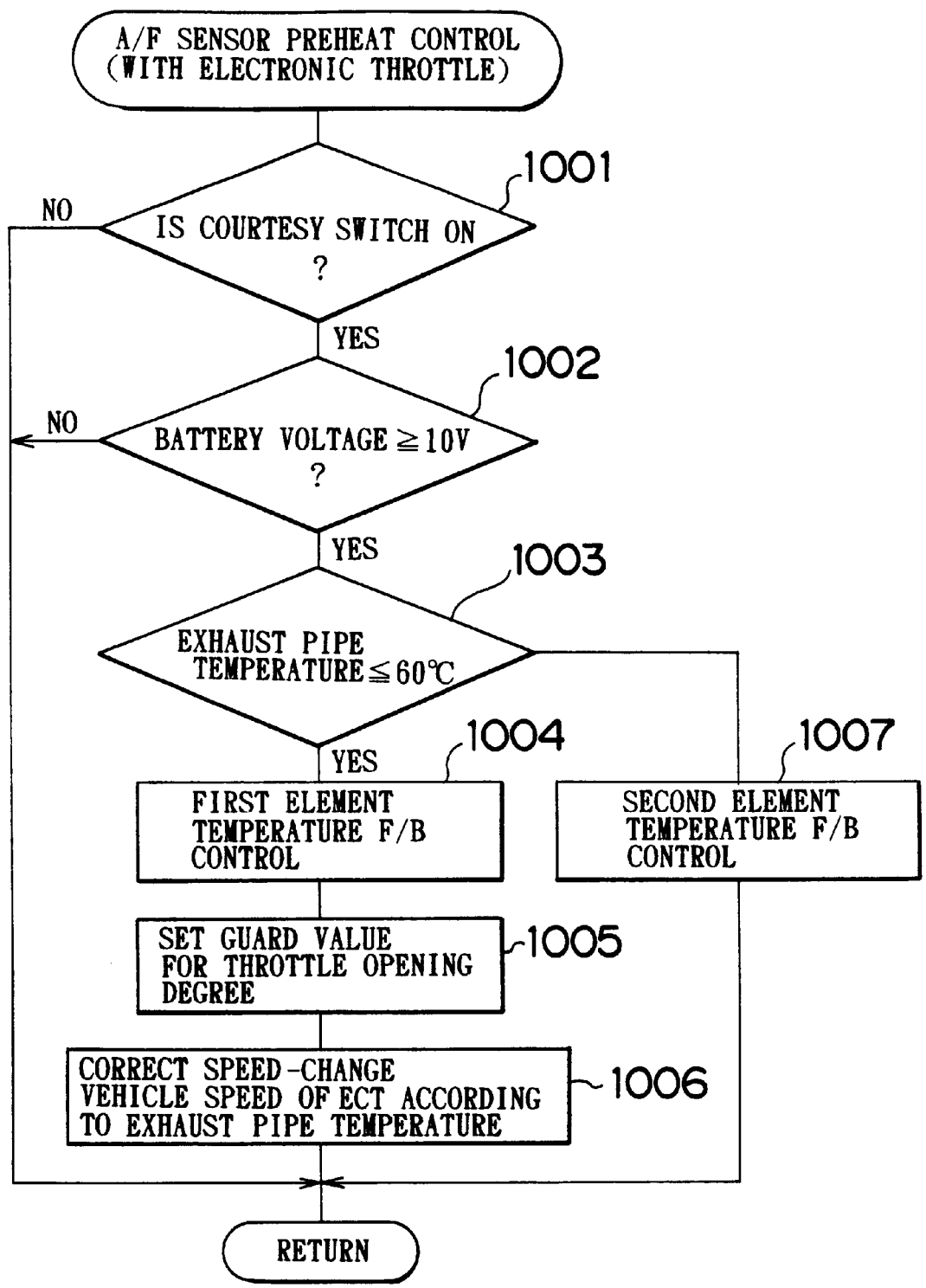
FIG. 13 is a flowchart of an exemplary preheat control routine of an air-fuel ratio sensor in an engine having an electronic throttle.

FIG. 10 is a flowchart of an exemplary embodiment of a heater control routine. In the flowchart shown in FIG. 10, if the result is NO in step 403 of the flowchart shown in FIG. 4, processing in steps 705 and 706 of FIG. 10 are carried out. Processing in the present routine and in flowcharts shown in FIGS. 11 through 13 are carried out at intervals of a predetermined period, for example, 64 ms. First of all, it is determined in step 401 whether an ignition switch (IGSW) 46 is on or off. If the IGSW 46 is on, the operation proceeds to step 402. If the IGSW 46 is off, the present routine is terminated.

Processing in steps 402 through 412 will now be described. For early activation of the air-fuel ratio sensor 1, the battery 5 starts supplying electric power to the heater 4, and electric power set in accordance with duty control at the time of engine starting operation is supplied to the heater 4 until the heater temperature reaches a predetermined temperature (engine-starting DUTY control). If the heater temperature reaches the predetermined temperature, electric power corresponding to the heater temperature is supplied to the heater 4 (heater upper limit resistance F/B control). If the temperature of the air-fuel ratio sensor 1 reaches a predetermined temperature, electric power for maintaining an activated state of the sensor element 2 in accordance with an element temperature of the air-fuel ratio sensor 1 is supplied to the heater 4 (element temperature F/B control). Next, the processing in steps 402 through 412 will be described individually.

In step 402, an element direct-current impedance Zdc of the air-fuel ratio sensor 1 is calculated. The impedance Zdc is calculated by detecting an electric current Ineg at the time of application of a negative voltage Vneg to the sensor element 2 according to a formula Zdc=Vneg/Ineg. In general, the element direct-current impedance decreases in accordance with a rise in element temperature. For example, if the sensor element 2 has an activation temperature of 700° C., the element direct-current impedance is 30Ω.

It is determined in step 403 whether or not an activation flag F1 of the air-fuel ratio sensor 1 has been set. If F1=1, the operation proceeds to step 404 where the element temperature F/B control described in step 404 is performed. If F1=0, the operation proceeds to step 705.

In step 705, the temperature of the exhaust pipe is calculated. An exhaust pipe temperature calculating routine will be described below in detail with reference to FIG. 11. It is determined in step 706 whether or not the exhaust pipe temperature $T_{EP}$ is equal to or higher than a threshold value $T_{th}$. If $T_{EP} \geq T_{th}$, it is determined that water drops adhering to the inner wall surface of the exhaust pipe have evaporated, and the operation proceeds to step 405. By the processing in steps 405 through 412, the air-fuel ratio sensor 1 is heated at an early stage. If $T_{EP} < T_{th}$, it is determined that water drops have adhered to the inner wall surface of the exhaust pipe, or that it is quite likely that water drops may adhere to the inner wall surface of the exhaust pipe. That is, it is determined that there is a possibility of the sensor element being damaged through wetting. Thus, the present routine is terminated and the air-fuel ratio sensor 1 is prevented from being heated at an early stage.

In step 405, it is determined based on an element direct-current impedance whether or not the sensor element 2 has been activated. That is, if Zdc≦30Ω, it is determined that the sensor element 2 has been activated, and the activation flag F1 of the air-fuel ratio sensor 1 is set to 1 in step 406. Then in step 404, the element temperature F/B control is performed. If Zdc>30Ω, it is determined that the sensor element 2 has not been activated, and the operation proceeds to step 407 where the heater control for activation of the sensor element 2 is performed. The flag F1 is reset by a one-shot pulse signal when the ignition switch IGSW 66 is switched from off to on.

In step 407, an electric voltage Vn applied to the heater 4 and an electric current In flowing through the heater 4 are detected.

In step 408, a resistance Rh of the heater 4 is calculated according to the following formula: Rh=Vn/In.

It is determined in step 409 whether or not the heater temperature is below a heater upper limit temperature, such as, for example, 1020° C., which is lower than a heat-resistant threshold temperature, such as, for example, 1200° C., by a predetermined temperature. If the result in step 409 is YES, the operation proceeds to step 410 where DUTY control for supplying the greatest possible electric power to the heater 4 is performed. If the result in step 409 is NO, the operation proceeds to step 411 where control for maintaining the heater 4 at the heater upper limit temperature of 1020° C. is performed. The processing in step 412 and step 413 are the same as those of the first embodiment and thus will not be described.

Figure 11:
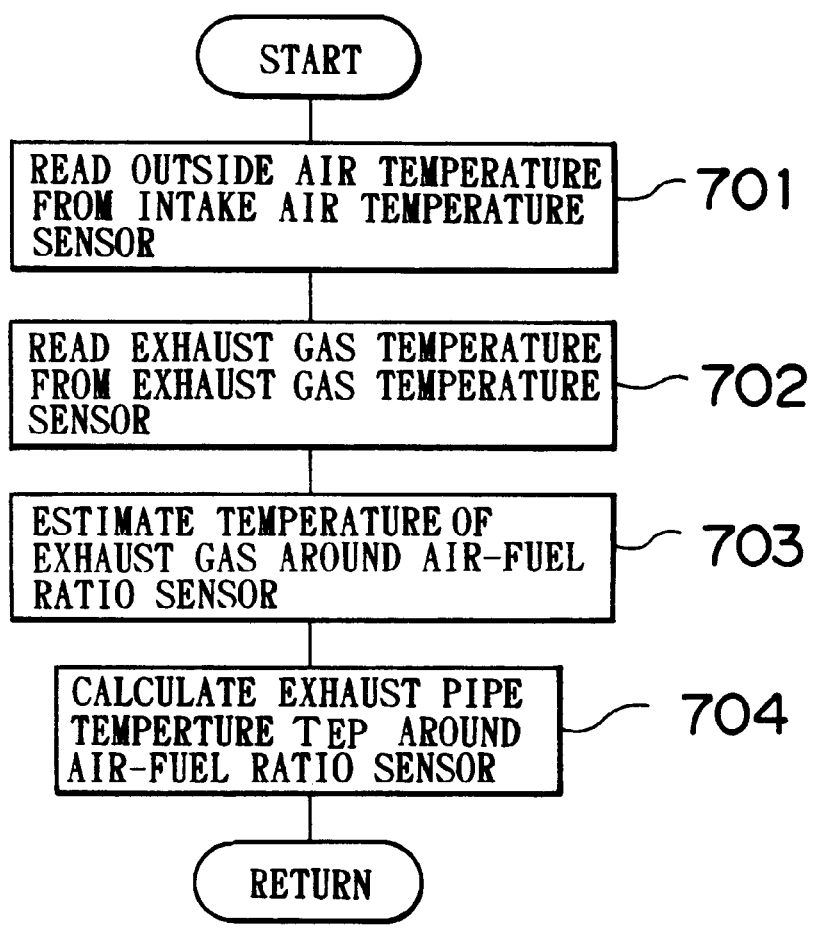
FIG. 11 is a flowchart of an exemplary exhaust pipe temperature calculating routine according to the second embodiment of the present invention.

FIG. 11 is a flowchart of an exhaust pipe temperature calculating routine. In step 701, an outside air temperature $T_{OA}$ detected by the intake air temperature sensor 56 is read. In step 702, an exhaust gas temperature $T_{EA2}$ exactly under the main catalyst 63, which is detected by the exhaust gas temperature sensor 64, is read. In step 703, an exhaust gas temperature $T_{EA1}$ in the vicinity of the air-fuel ratio sensor 1 is estimated from the outside air temperature $T_{OA}$ and the exhaust gas temperature $T_{EA2}$ in the following manner.

A decrease $T_D$ in exhaust gas temperature from the vicinity of the air-fuel ratio sensor 1 to the vicinity of the exhaust gas temperature sensor 64 is estimated from the outside air temperature $T_{OA}$ and a heat transfer rate k1 of the exhaust pipe. The exhaust gas temperature $T_{EA1}$ is obtained by adding the decrease $T_D$ in exhaust gas temperature to the exhaust gas temperature $T_{EA2}$. Therefore, the following formula is established:

$$T_{EA1} = T_{EA2} + T_D \ldots \quad (1)$$

In step 704, the exhaust pipe temperature $T_{EP}$ around the air-fuel ratio sensor 1 is calculated from the exhaust gas temperature $T_{EA1}$ in the vicinity of the air-fuel ratio sensor 1 calculated in step 703, and a heat transfer rate k2 of the exhaust pipe with respect to air.

The exhaust pipe temperature $T_{EP}$ can also be calculated as follows. First, the exhaust gas temperature $T_{EA1}$ in the vicinity of the air-fuel ratio sensor 1 is calculated from a two-dimensional map of the engine rotational speed NE detected by the rotational speed sensor 67 and an intake air amount GA detected by an airflow meter (not shown). This two-dimensional map is made up of experimental values. The higher the engine rotational speed NE becomes, the higher the exhaust gas temperature $T_{EA1}$ becomes. The exhaust pipe temperature $T_{EP}$ is calculated from the thus-calculated exhaust gas temperature $T_{EA1}$ and the outside air temperature $T_{OA}$ detected by the intake air temperature sensor 56 according to the following formula:

$$T_{EP} = \alpha(T_{EA1-TOA})$$

In this formula, α is a constant.

In preheat control of the air-fuel ratio sensor, before the engine is started by the ignition key and after the driver has opened the door on the side of the driver's seat and sat in the seat, activation of the air-fuel ratio sensor 1 is started immediately after the closing of the door by the driver. An example wherein the preheat control is applied to an engine that is not equipped with an electronic throttle will be described with reference to FIG. 12. An example wherein the preheat control is applied to an engine that is equipped with an electronic throttle will be described with reference to FIG. 13.

FIG. 12 is a flowchart of a preheat control routine of the air-fuel ratio sensor. First, it is determined in step 901 whether or not the driver is seated in the driver's seat after the turning-on of a courtesy switch (not shown), that is, a door switch on the side of the driver's seat. If the result in step 901 is YES, the operation proceeds to step 902. If the result in step 901 is NO, the present routine is terminated. It is determined in step 902 whether or not an electric voltage VB of the battery 5 has become equal to or higher than 10 V. If $V_B \geq 10$ V, the operation proceeds to step 903. If $V_B < 10$ V, the present routine is terminated.

It is determined in step 903 whether or not the exhaust gas temperature $T_{EP}$ calculated by carrying out the exhaust gas temperature calculating routine shown in FIG. 11 has exceeded a dew point of 60° C. If $T_{EP} \leq 60$ ° C., it is determined that the sensor element may be damaged through wetting due to the evaporation of water sticking to the inner wall surface of the exhaust pipe. Thus, the operation proceeds to step 904 where first element temperature F/B control for maintaining the element temperature of the air-fuel ratio sensor at about 350° C. is performed. If $T_{EP} > 60$ ° C., it is determined that the water adhering to the inner wall surface of the exhaust pipe has evaporated and that the sensor element is unlikely to be damaged through wetting. Thus, the operation proceeds to step 905 where second element temperature F/B control for maintaining the element temperature of the air-fuel ratio sensor at about 700° C. is performed. During the first element temperature F/B control, the air-fuel ratio sensor 1 is used for air-fuel ratio control as a λ-type $O_2$ sensor. During the second element temperature F/B control, the air-fuel ratio sensor 1 is used for wide range air-fuel ratio control as an oxygen concentration detecting element of a limiting current type. In the first and second element temperature F/B control, an element direct-current impedance Zdc is calculated, and the same control as in step 404 of FIG. 10 is performed.

FIG. 13 is a flowchart of a preheat control routine of the air-fuel ratio sensor in the engine that is equipped with the electronic throttle. First, it is determined in step 1001 whether or not the driver is seated in the driver's seat after the turning-on of a courtesy switch (not shown), that is, a door switch on the side of the driver's seat. If the result in step 1001 is YES, the operation proceeds to step 1002. If the result in step 1001 is NO, the present routine is terminated. It is determined in step 1002 whether or not an electric voltage VB of the battery 5 has become equal to or higher than 10 V. If $V_B \geq 10$ V, the operation proceeds to step 1003. If $V_B < 10$ V, the present routine is terminated.

It is determined in step 1003 whether or not the exhaust gas temperature $T_{EP}$ calculated by carrying out the exhaust gas temperature calculating routine shown in FIG. 11 has exceeded a dew point of 60° C. If $T_{EP} \leq 60$ ° C., it is determined that the sensor element may be damaged through wetting due to the evaporation of water adhering to the inner wall surface of the exhaust pipe. Thus, the operation proceeds to steps 1004 through 1006. In step 1004, first element temperature F/B control for maintaining the element temperature of the air-fuel ratio sensor at about 380° C. is performed. If $T_{EP} > 60$ ° C., it is determined that the water adhering to the inner wall surface of the exhaust pipe has evaporated and that the sensor element is unlikely to be damaged through wetting. Thus, the operation proceeds to step 1007 where second element temperature F/B control for maintaining the element temperature of the air-fuel ratio sensor at about 700° C. is performed.

Figure 14:
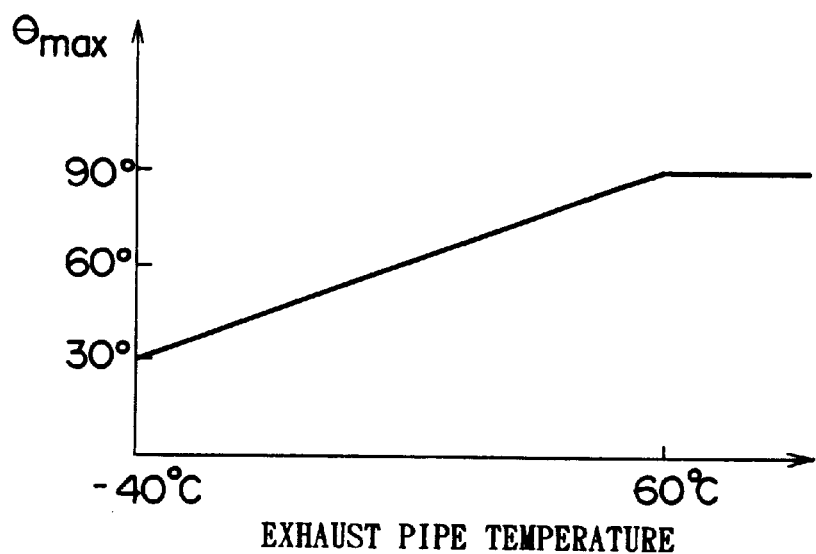
FIG. 14 illustrates the relationship between exhaust pipe temperature and throttle opening degree guard value.

In step 1005, a guard value θmax for an opening degree of the throttle valve is set in accordance with an exhaust pipe temperature $T_{EP}$ based on a map shown in FIG. 14. Then in step 1006, a vehicle speed (hereinafter referred to as the speed-change vehicle speed) at the time of an automatic speed-change operation from a first speed (Low) to a second speed (2nd), from the second speed to a third speed (3rd), or from the third speed (3rd) to a fourth speed (4th) performed by an ECT (Electronically Controlled Transmission), by an automatic transmission, is corrected in accordance with the exhaust pipe temperature $T_{EP}$ based on a map shown in FIG. 15.

An example of a control program for speed-change ratios of the automatic transmission will now be described briefly. The vehicle is accelerated by increasing the opening degree of the throttle valve from 0° to 50°. As soon as the vehicle speed reaches 50 km/h, the opening degree of the throttle valve is reduced to 10° and the vehicle makes a transition to a normal running state. At the time of acceleration, if the opening degree of the throttle valve is reduced by 10° during the speed-change operation from the first speed (Low) to the second speed (2nd), the speed-change operation from the second speed (2nd) to the third speed (3rd) is performed. Meanwhile, the engine rotational speed rises with the lapse of time during acceleration of the vehicle but falls during the speed-change operation. If the vehicle speed at the time of the speed-change operation from the first speed (Low) to the second speed (2nd) is reduced, it takes longer for the vehicle speed to reach 50 km/h, and the accelerating performance deteriorates. However, in the period of acceleration from 0 km/h to 50 km/h, fuel consumption improves.

FIG. 14 is a two-dimensional map of exhaust pipe temperature versus throttle opening degree guard value. As shown, the axis of the abscissa represents the exhaust pipe temperature $T_{EP}$(° C.), and the axis of the ordinate represents the guard value θmax (°) for the opening degree of the throttle valve. Until the temperature of the exhaust pipe reaches 60° C., it is determined that the sensor element may be damaged through wetting. Thus, in order to reduce the flow rate of exhaust gas, the guard value θmax for the opening degree of the throttle valve is set to a value smaller than usual, for example, to 30° to 90°. The amount of intake air of the engine is reduced and the engine rotational speed is made lower than usual, so that the flow rate of exhaust gas is reduced. By reducing the flow rate of exhaust gas, water drops adhering to the inner wall of the exhaust pipe are inhibited from splashing, whereby the sensor element is prevented from being wetted.

On the other hand, if the temperature of the exhaust pipe becomes equal to or higher than 60° C., it is determined that the water drops adhering to the inner wall of the exhaust pipe have evaporated. Thus, the guard value Oman for the opening degree of the throttle valve is set to a usual value of 90°, whereby the control for reducing a flow rate of exhaust gas is stopped.

Figure 15:
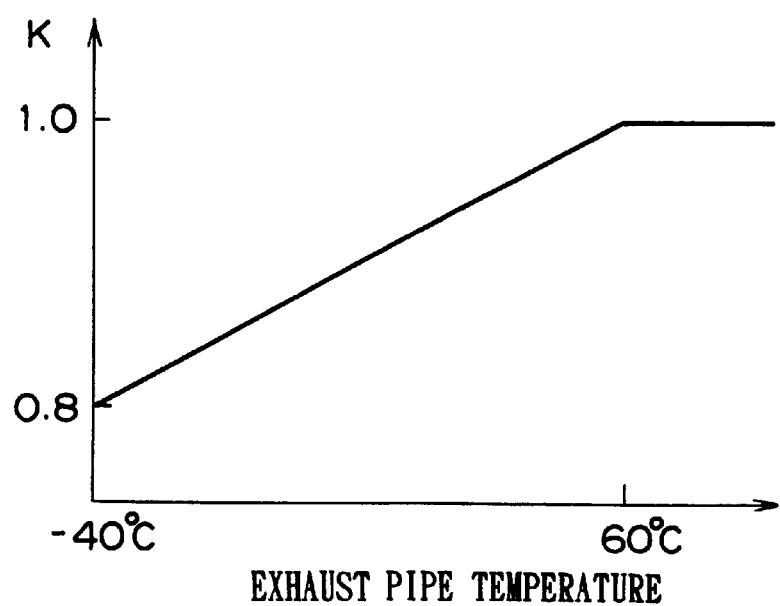
FIG. 15 illustrates the relationship between exhaust pipe temperature and speed-change vehicle speed correction factor.

FIG. 15 is a two-dimensional map of exhaust pipe temperature versus speed-change vehicle speed correction factor. Referring to FIG. 15, the axis of the abscissa represents the exhaust pipe temperature $T_{EP}$(° C.), and the axis of the ordinate represents the speed-change vehicle speed correction factor k. Until the temperature of the exhaust pipe reaches 60° C., it is determined that the sensor element may be damaged through wetting. Thus, the speed-change vehicle speed correction factor k is set to a value of 0.8 to 1.0 and the engine rotational speed is made lower than usual, whereby the flow rate of exhaust gas is reduced. By reducing the flow rate of exhaust gas, water drops adhering to the inner wall of the exhaust pipe are inhibited from splashing, whereby the sensor element is prevented from being wetted.

On the other hand, if the temperature of the exhaust pipe becomes equal to or higher than 60° C., it is determined that the water drops adhering to the inner wall of the exhaust pipe have evaporated. Thus, the speed-change vehicle speed correction factor k is set to 1.0 and the engine rotational speed is set to a normal speed, whereby the control for reducing a flow rate of exhaust gas is stopped.

The speed-change vehicle speed correction factor k is a factor for correcting a vehicle speed at the time of an automatic speed-change operation from the first speed (Low) to the second speed (2nd), from the second speed to the third speed (3rd) or from the third speed to the fourth speed (4th) performed by the automatic transmission. For example, when the speed-change operation from the second speed (2nd) to the third speed (3rd) is performed, the vehicle speed is 30 km/h if k=1.0, and the vehicle speed is 24km/h if k=0.8.

According to the above-described second embodiment of the present invention, when electric power is supplied to the heater of the air-fuel ratio sensor during preheating of the air-fuel ratio sensor during or prior to the cold starting operation of the engine, the possibility of the element of the air-fuel ratio sensor being wetted is determined based on whether or not water has adhered to the wall surface of the exhaust pipe. If it is determined that water has adhered to the wall surface of the exhaust pipe, the electric power supplied to the heater is limited. Therefore, it is possible to prevent the element of the air-fuel ratio sensor from cracking due to thermal shock resulting from the wetting of the sensor element.

While the present invention has been described in detail with reference to preferred embodiments thereof, it is to be understood that the present invention is not limited to the disclosed embodiments or constructions. On the contrary, the present invention is intended to cover various modifications and equivalent arrangements. In addition, while the various elements of the disclosed invention are shown in various combinations and configurations which are exemplary, other combinations and configurations, including more, less or only a single embodiment, are also within the spirit and scope of the present invention.

What is claimed is:

1. An oxygen concentration detector, comprising:
   an air-fuel ratio sensor;
   a heater that heats the air-fuel ratio sensor;
   a heater controller that supplies electric power to the heater such that the air-fuel ratio sensor reaches an activation temperature; and
   an element temperature detector that detects a temperature of an element of the air-fuel ratio sensor;
   wherein the heater controller detects a rate of decrease in the temperature of the element of the air-fuel ratio sensor based on the temperature of the element detected by the element temperature detector, and controls the supply of electric power to the heater so as to attenuate thermal shock of the element when the rate of decrease in the temperature of the element is greater than a reference value.

2. The oxygen concentration detector according to claim 1, wherein the element temperature detector detects the temperature of the element of the air-fuel ratio sensor based on an impedance of the element.

3. The oxygen concentration detector according to claim 1, wherein the heater controller prevents the heater from being supplied with electric power so as to attenuate thermal shock of the element.

4. In combination:
   an internal combustion engine comprising an exhaust passage; and
   an oxygen concentration detector according to claim 1, wherein the air-fuel ratio sensor is provided in the exhaust passage of the internal combustion engine.

5. An oxygen concentration detector, comprising:
   an air-fuel ratio sensor;
   a heater that heats the air-fuel ratio sensor; and
   a heater controller that supplies electric power to the heater such that the air-fuel ratio sensor reaches an activation temperature;
   wherein the heater controller predicts whether an element of the air-fuel ratio sensor may be wetted, and limits the supply of electric power to the heater when wetting of the element is predicted.

6. The oxygen concentration detector according to claim 5, wherein the air-fuel ratio sensor is located in an exhaust passage of an internal combustion engine, and further comprising a flow rate controller that reduces a flow rate of exhaust gas in the internal combustion engine when the wetting of the element of the air-fuel ratio sensor is predicted.

7. The oxygen concentration detector according to claim 5, wherein the heater controller determines whether water is disposed on a wall surface of an exhaust passage to which the air-fuel ratio sensor is attached.

8. The oxygen concentration detector according to claim 7, wherein the heater controller determines that the sensor element may be wetted, when the heater controller determines that water is disposed on the wall surface of the exhaust passage.

9. The oxygen concentration detector according to claim 7, further comprising a flow rate controller that reduces a flow rate of exhaust gas in the internal combustion engine when the heater controller determines that water is disposed on the wall surface of the exhaust passage.

10. The oxygen concentration detector according to claim 7, wherein the heater controller determines, based on a temperature of the exhaust passage, whether water is disposed on the wall surface of the exhaust passage.

11. In combination:
    an internal combustion engine comprising an exhaust passage; and
    an oxygen concentration detector according to claim 5, wherein the air-fuel ratio sensor is disposed in the exhaust passage of the internal combustion engine.

12. A method of attenuating thermal shock of an element of an air-fuel ratio sensor disposed in an exhaust passage of an internal combustion engine, the method comprising:
    supplying electric power to a heater so as to heat the air-fuel ratio sensor disposed in the exhaust passage of the internal combustion engine to an activation temperature;
    detecting the temperature of the element of the air-fuel ratio sensor;
    detecting a rate of decrease in the temperature of the element of the air-fuel ratio sensor;
    determining, when the rate of decrease in the temperature of the element is greater than a reference value, that the element has been wetted; and
    controlling the supply of electric power to the heater so as to attenuate thermal shock of the element.

13. The method according to claim 12, wherein the temperature of the element of the air-fuel ratio sensor is detected based on an impedance of the element.

14. The method according to claim 12, wherein the supply of electric power to the heater is stopped when the sensor element is determined to have been wetted.

15. A method of attenuating thermal shock of an element of an air-fuel ratio sensor disposed in an exhaust passage of an internal combustion engine, the method comprising:

supplying electric power to a heater so as to heat the air-fuel ratio sensor provided in the exhaust pipe of the internal combustion engine to an activation temperature;

determining whether an element of the air-fuel ratio sensor may be wetted; and limiting the supply of electric power to the heater when it is determined that the element of the sensor may be wetted.

16. The method according to claim 15, further comprising reducing a flow rate of exhaust gas in the internal combustion engine when it is determined that the element of the sensor may be wetted.

17. The method according to claim 15, wherein the determining includes determining whether water is disposed on a wall surface of the exhaust passage.

18. The method according to claim 17, further comprising reducing a flow rate of exhaust gas in the internal combustion engine when it is determined that water is disposed on the wall surface of the exhaust pipe.

19. The method according to claim 17, wherein the determination as to whether water is disposed on a wall surface of the exhaust pipe is based on a temperature of the exhaust pipe.

* * * * *